United States Patent
Scheinblum et al.

(10) Patent No.: US 12,138,155 B2
(45) Date of Patent: *Nov. 12, 2024

(54) CRIMPING ACCESSORY DEVICE FOR A PROSTHETIC VALVE

(71) Applicant: Edwards Lifesciences Corporation, Irvine, CA (US)

(72) Inventors: Taylor Jacob Scheinblum, Newport Beach, CA (US); Mindy Lee Ann Black, Huntington Beach, CA (US); Tamir S. Levi, Zikhron Yaakov (IL); Evan T. Schwartz, Huntington Beach, CA (US); Waina Michelle Chu, Tustin, CA (US); Linda Thai, Mission Viejo, CA (US); Hanoch Cohen-Tzemach, Holon (IL); Michael Bukin, Pardes Hanna (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 557 days.

This patent is subject to a terminal disclaimer.

(21) Appl. No.: 17/228,446

(22) Filed: Apr. 12, 2021

(65) Prior Publication Data
US 2021/0228343 A1 Jul. 29, 2021

Related U.S. Application Data

(63) Continuation of application No. 15/809,915, filed on Nov. 10, 2017, now Pat. No. 10,973,631.
(Continued)

(51) Int. Cl.
*A61F 2/24* (2006.01)
*A61F 2/95* (2013.01)
*B25B 27/02* (2006.01)

(52) U.S. Cl.
CPC .......... *A61F 2/2412* (2013.01); *A61F 2/2403* (2013.01); *A61F 2/2427* (2013.01);
(Continued)

(58) Field of Classification Search
CPC .... A61F 2/9524; A61F 2/9525; A61F 2/9526; A61F 2/2427; A61F 2/243; A61F 2/2403;
(Continued)

(56) References Cited

U.S. PATENT DOCUMENTS 3,409,013 A 11/1968 Berry
3,548,417 A 12/1970 Kisher
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Diane D Yabut
*Assistant Examiner* — Christina C Lauer
(74) *Attorney, Agent, or Firm* — Klarquist Sparkman, LLP; Joel B. German

(57) ABSTRACT

Embodiments are provided of an assembly having a prosthetic valve, the prosthetic valve having a radially expandable and compressible annular frame, and a crimping accessory device, and methods for using the assembly in compressing the prosthetic valve. The frame includes an outer surface and an inner surface. A leaflet assembly is supported inside the annular frame. The leaflet assembly
(Continued)

includes a plurality of leaflets, each having an inner surface and an outer surface. The crimping accessory device has a plurality of axially-extending fingers. At least a first finger of the plurality of fingers is disposed between the outer surface of a first leaflet of the plurality of leaflets, and at least a second finger of the plurality of fingers is disposed radially-inwardly of the inner surface of the first leaflet.

17 Claims, 11 Drawing Sheets

Related U.S. Application Data

(60) Provisional application No. 62/423,675, filed on Nov. 17, 2016.

(52) U.S. Cl.
CPC .......... *A61F 2/2433* (2013.01); *A61F 2/2415* (2013.01); *A61F 2/2418* (2013.01); *A61F 2/2454* (2013.01); *A61F 2/95* (2013.01); *A61F 2/9522* (2020.05); *B25B 27/02* (2013.01)

(58) Field of Classification Search
CPC ........ A61F 2/2412; A61F 2/2407; A61F 2/95; A61F 2002/9522; A61F 2230/005
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |

(56) References Cited

U.S. PATENT DOCUMENTS

| | | |
|---|---|---|
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Fidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 10,973,631 B2 * | 4/2021 | Scheinblum ........ A61F 2/2412 |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288775 A1 | 12/2005 | Dong |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 * | 6/2008 | Benichou ........... A61F 2/2418 623/1.26 |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0179649 A1 * | 7/2010 | Richter ............... A61F 2/2409 623/2.11 |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0004299 A1 | 1/2011 | Essinger et al. |
| 2011/0015729 A1 | 1/2011 | Jimenez et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222135 A1 * | 8/2014 | Forster ............... A61F 2/2439 623/2.11 |
| 2014/0222136 A1 | 8/2014 | Geist et al. |
| 2014/0277417 A1 | 9/2014 | Schraut et al. |

(56) References Cited

U.S. PATENT DOCUMENTS

| | | |
|---|---|---|
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0128819 A1* | 5/2016 | Giordano .............. A61F 2/2427 623/2.11 |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2010139340 A1 | 12/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

* cited by examiner

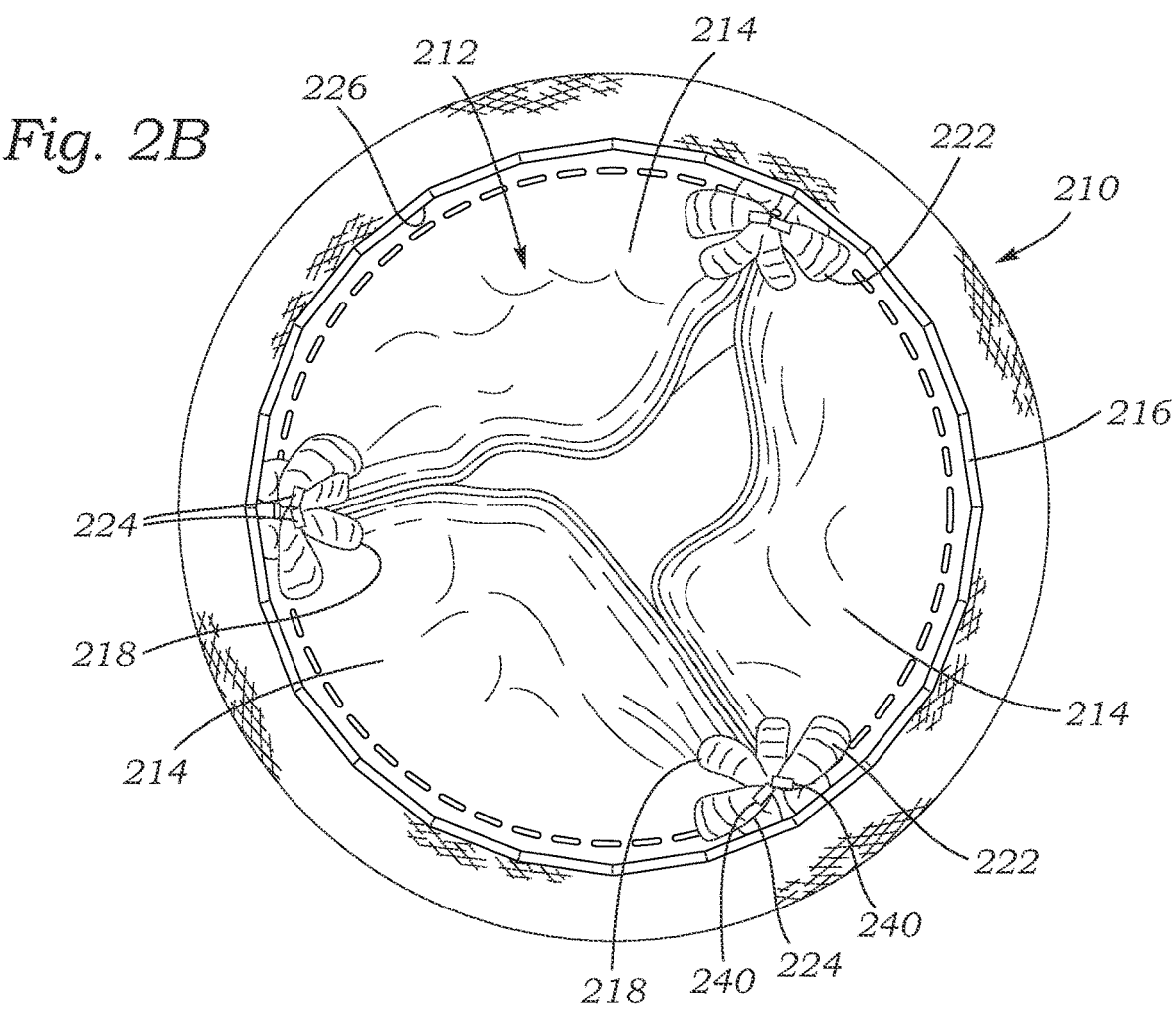

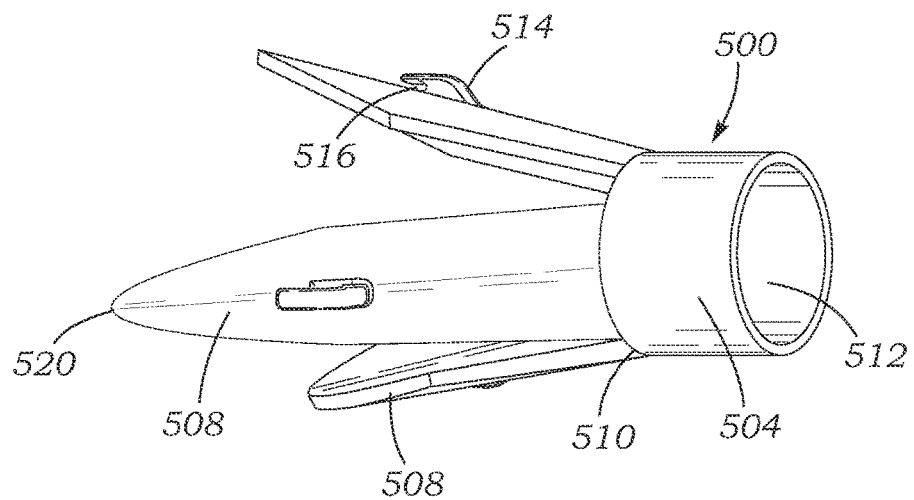
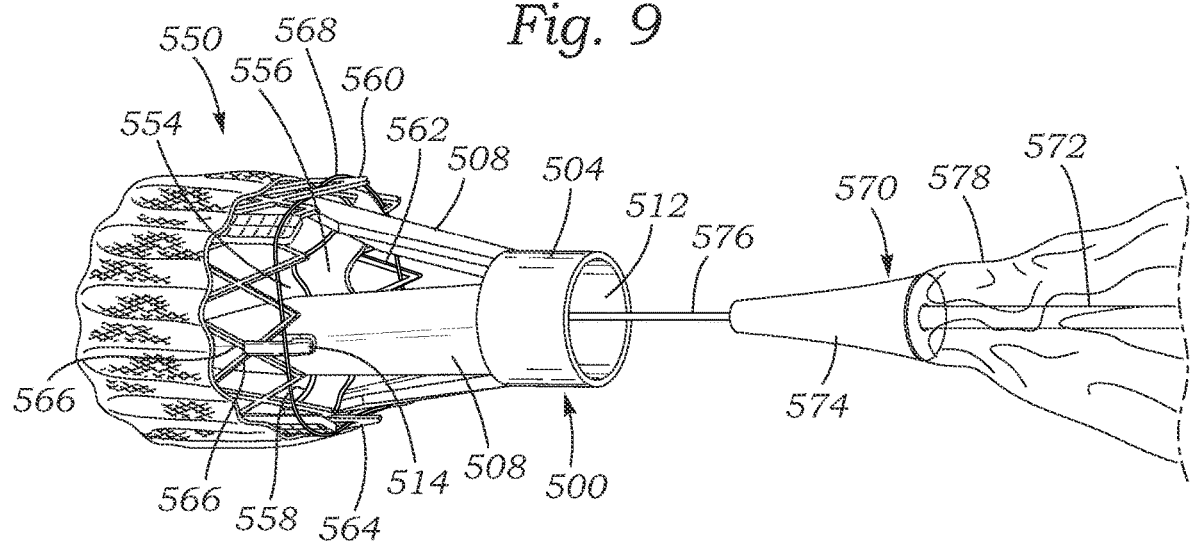

CRIMPING ACCESSORY DEVICE FOR A PROSTHETIC VALVE

CROSS-REFERENCE TO RELATED APPLICATIONS

This application is a continuation of U.S. patent application Ser. No. 15/809,915, filed Nov. 10, 2017, which in turn claims the benefit of U.S. Provisional Patent Application No. 62/423,675, filed Nov. 17, 2016. Each of these applications is hereby incorporated by reference herein.

FIELD

The present disclosure relates to a crimping accessory device that can be used with a prosthetic valve. More particularly, the present disclosure relates to embodiments of a crimping accessory device that can be used to protect valve leaflets while the prosthetic valve is crimped with a crimping apparatus from a large diameter to a smaller diameter.

BACKGROUND

In recent years, a variety of prosthetic valves have been developed wherein a valve structure (e.g., tissue leaflets) is mounted on a metal stent and then delivered to a treatment site via a catheterization technique. Such transcatheter prosthetic valves may be self-expandable or balloon-expandable. Balloon-expandable prosthetic valves are typically crimped from an initial large diameter to a smaller diameter prior to advancement to a treatment site in the body. Before crimping, a balloon-expandable prosthetic valve is typically placed over an inflatable balloon on a catheter shaft. Once delivered to the implantation site, the balloon can be inflated to expand the prosthetic valve to its fully functional size. Self-expanding prosthetic valves are typically also crimped to a smaller diameter, and are then inserted into a sheath. After placement in the body, the sheath is withdrawn, and the prosthetic valve expands inside the body.

A known type of crimping apparatus for crimping a prosthetic valve includes a plurality of circumferentially arranged moveable segments that define a variable diameter crimping aperture. When a prosthetic valve is placed in the crimping aperture, the moveable segments are moved radially inwardly to decrease the diameter of the crimping aperture, thereby radially compressing the prosthetic valve. In some cases, during the crimping process, the leaflets can become damaged by contacting the metal stent, or components of the prosthetic valve can be deformed.

SUMMARY

The present disclosure pertains to embodiments of a crimping accessory device and embodiments of a method for its use in crimping expandable stents or prosthetic valves having a radially expandable and compressible annular body. In an exemplary embodiment, the present disclosure provides an assembly comprising a prosthetic valve comprising a radially expandable and compressible annular frame. The frame has an outer surface and an inner surface. A leaflet assembly is supported inside the annular frame. The leaflet assembly comprises a plurality of leaflets, each having an inner surface and an outer surface. The assembly further comprises a crimping accessory device comprising an elongate shaft and a plurality of axially-extending fingers. At least a first finger of the plurality of fingers is disposed between the outer surface of a first leaflet of the plurality of leaflets and the inner surface of the frame. At least a second finger of the plurality of fingers is disposed radially inwardly of the inner surface of the first leaflet.

In another representative embodiment, the present disclosure provides an assembly comprising a prosthetic valve comprising a radially expandable and compressible annular frame. The frame has an outer surface and an inner surface. A leaflet assembly is supported inside the annular frame. The leaflet assembly comprises a plurality of leaflets, each leaflet having an inner and an outer surface. The assembly further comprises a crimping accessory device comprising an elongate shaft and at least one axially-extending finger disposed between the inner surface of the frame and an outer surface of a leaflet of the plurality of leaflets. The at least one finger comprises a hook formed on the outer surface of the finger.

In a further representative embodiment, the present disclosure provides an assembly comprising a prosthetic valve comprising a radially expandable and compressible annular frame. The frame comprises an outer surface and an inner surface, and defines a plurality of windows. The prosthetic valve further comprises a leaflet assembly supported inside the annular frame. The leaflet assembly comprises a plurality of leaflets, each having an inner surface and an outer surface. The assembly further comprises a crimping accessory device comprising an elongate shaft and at least one axially-extending finger having a proximal portion disposed between a proximal portion of the inner surface of the frame and a proximal portion of the outer surface of a leaflet of the plurality of leaflets. The at least one finger extends distally through, and radially outwardly from, a frame window.

Also disclosed herein is a method of using the disclosed assemblies to crimp a prosthetic valve in cooperation with the crimping accessory device. In some embodiments, the method comprises inserting at least one finger of the crimping accessory device between the inner surface of the annular frame and the outer surface of at least one leaflet of the leaflet assembly. The prosthetic valve is radially compressed. The crimping accessory is removed from the prosthetic valve.

In another aspect, the present disclosure provides a method for compressing a prosthetic valve in cooperation with a crimping accessory device. The prosthetic valve includes a radially expandable and compressible annular frame and a leaflet assembly mounted inside of the frame. The method includes inserting each of a first plurality of fingers of the crimping accessory device between an inner surface of the annular frame and an outer surface of a respective leaflet. A second plurality of fingers of the crimping accessory device are placed against an inner surface of a respective leaflet. The prosthetic valve is placed in a crimping aperture formed by a plurality of circumferentially-arranged jaws. The prosthetic valve is at least partially crimped, and the crimping accessory device is removed from the prosthetic valve.

The foregoing and other objects, features, and advantages of the disclosed technologies will become more apparent from the following detailed description, which proceeds with reference to the accompanying figures.

BRIEF DESCRIPTION OF THE DRAWINGS

FIG. 2B is a plan view of the outflow end of a prosthetic valve, showing the valve leaflets arranged asymmetrically about the circumference of the valve frame.

FIG. 8 is perspective view of an exemplary crimping accessory device having a plurality of fingers, with a hook extending from at least one of the fingers.

FIG. 9 is a perspective view of the crimping accessory device of FIG. 8 in use with a prosthetic valve.

DETAILED DESCRIPTION

Figure 1:
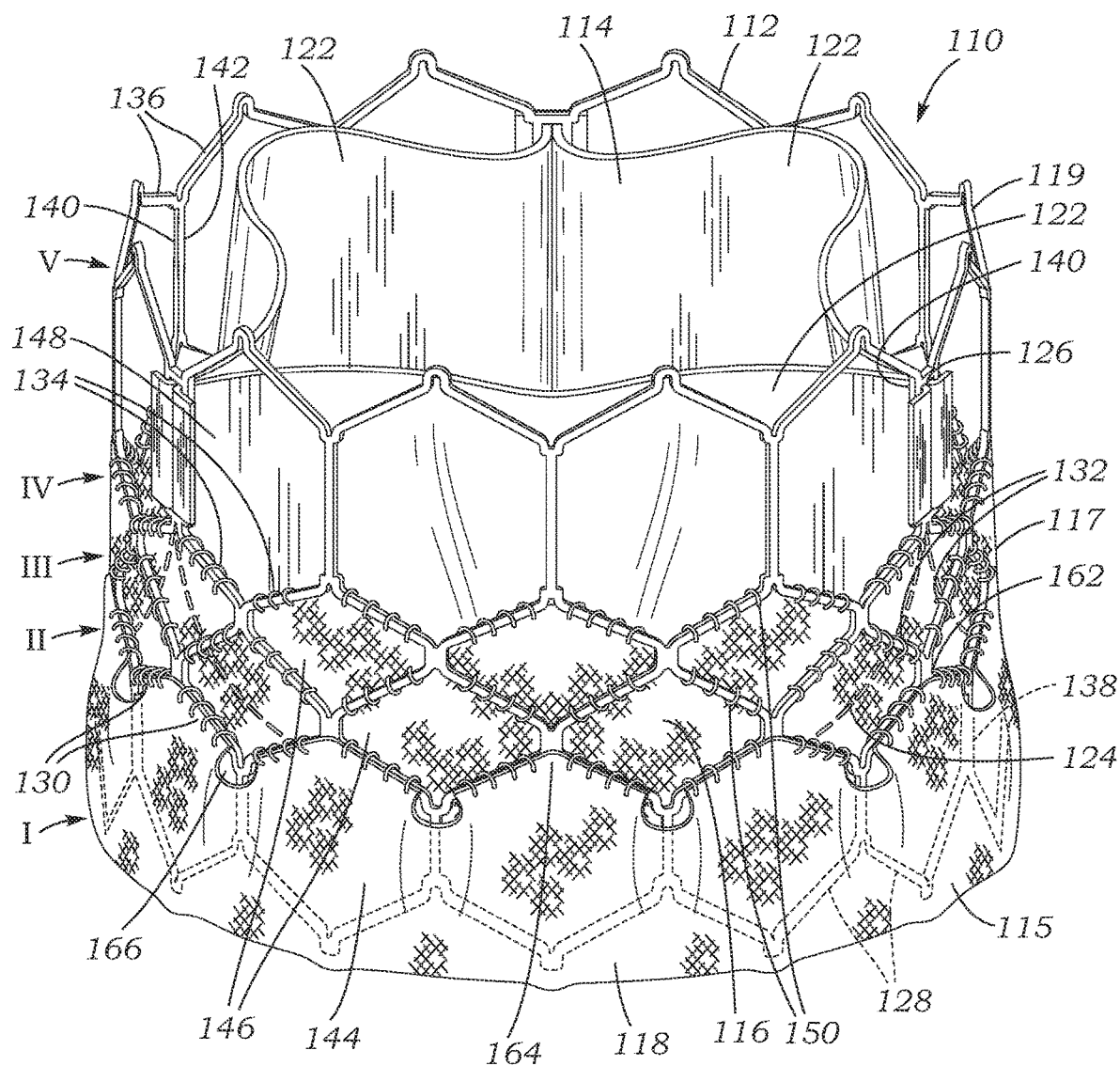
FIG. 1 is a perspective view of a prosthetic valve.

The present disclosure provides embodiments of a crimping accessory device for use with a prosthetic valve having a radially expandable and compressible annular frame. The crimping accessory device can be inserted into the prosthetic valve, and the prosthetic valve crimped to a smaller diameter. The crimping accessory device can help provide for more symmetrical crimping of the valve, as well as reducing the potential for damage to the valve during crimping. FIG. 1 illustrates an example prosthetic heart valve 110 with which embodiments of the disclosed crimping accessory device, such as the devices illustrated in FIGS. 3, 5, 8, and 10, can be used.

The illustrated prosthetic valve 110 is adapted to be implanted in the native aortic annulus, although in other embodiments it can be adapted to be implanted in the other native annuluses of the heart (e.g., the pulmonary, mitral, and tricuspid valves). The prosthetic valve 110 can also be adapted to be implanted in other tubular organs or passageways in the body. The prosthetic valve 110 can have four main components: a stent, or frame, 112, a valvular structure 114, an inner skirt 116, and a perivalvular sealing means, and can have an inflow end portion 115, an intermediate portion 117, and an outflow end portion 119. In the illustrated embodiment, the perivalvular sealing means comprises an outer skirt 118.

Figure 2A:
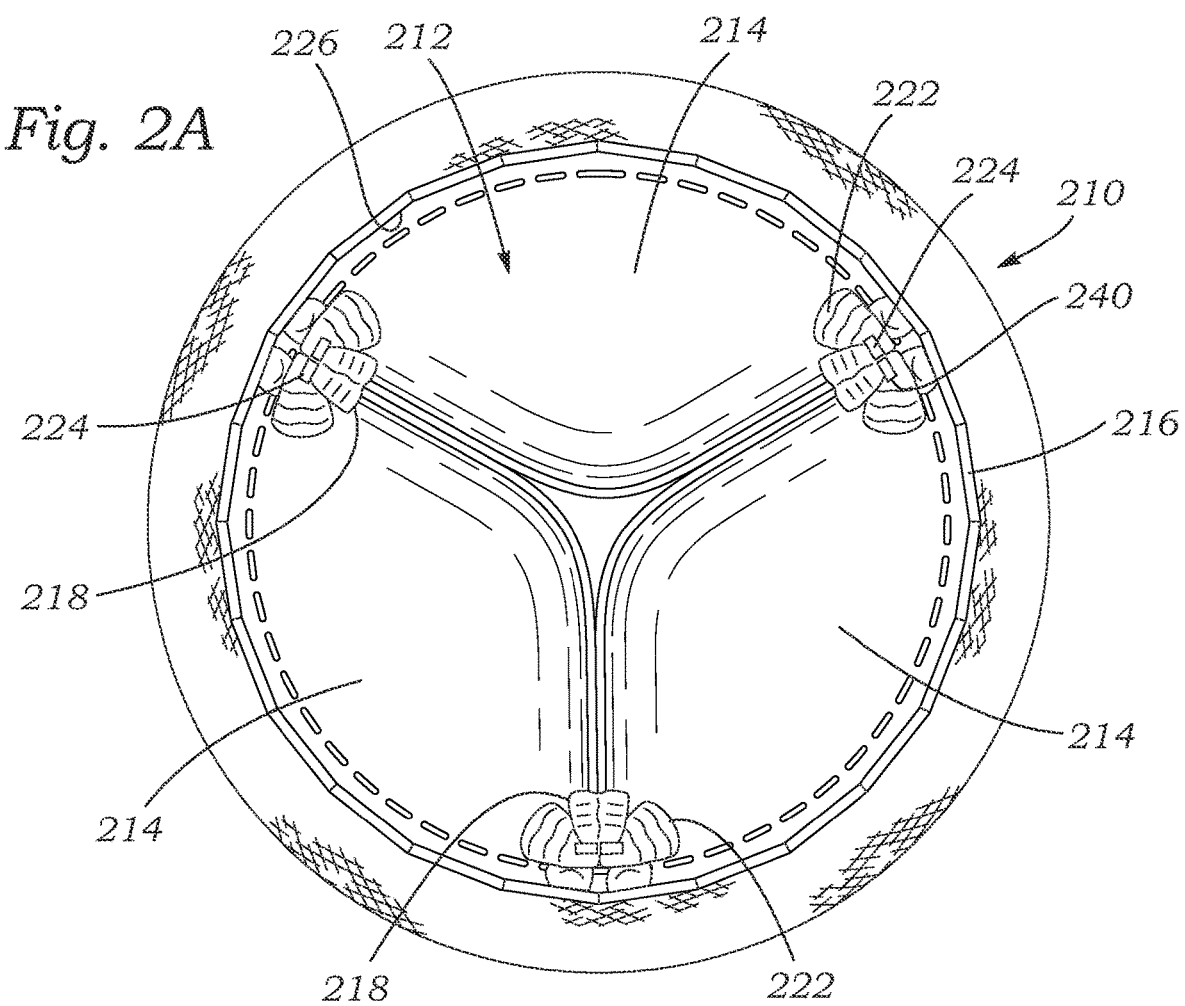
FIG. 2A is a plan view of the outflow end of a prosthetic valve, showing the valve leaflets arranged symmetrically about the circumference of the valve frame.

The valvular structure 114 can comprise three leaflets 122, collectively forming a leaflet structure, or assembly, which can be arranged to collapse in a tricuspid arrangement (analogous to the structure shown in FIG. 2A). The lower edge of the valvular structure 114 desirably has an undulating, curved scalloped shape (suture line 124 shown in FIG. 1 tracks the scalloped shape of the leaflet structure). By forming the leaflets 122 with this scalloped geometry, stresses on the leaflets are reduced, which in turn improves durability of the prosthetic valve 110.

Moreover, by virtue of the scalloped shape, folds and ripples at the belly of each leaflet 122 (the central region of each leaflet), which can cause early calcification in those areas, can be eliminated or at least minimized. The scalloped geometry also reduces the amount of tissue material used to form the leaflet structure, thereby allowing a smaller, more evenly crimped profile at the inflow end 115 of the prosthetic valve 110. The leaflets 122 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 112 can be formed with a plurality of circumferentially-spaced slots, or commissure windows 126 that are adapted to mount the commissures of the valvular structure 114 to the frame, as described in greater detail below. The frame 112 can be made of any of various suitable plastically-expandable materials (e.g., stainless steel, etc.) or self-expanding materials (e.g., nitinol) as known in the art. When constructed of a plastically-expandable material, the frame 112 (and thus the prosthetic valve 110) can be crimped to a radially collapsed configuration on a delivery catheter and then expanded inside a patient by an inflatable balloon or equivalent expansion mechanism. When constructed of a self-expandable material, the frame 112 (and thus the prosthetic valve 110) can be crimped to a radially collapsed configuration and restrained in the collapsed configuration by insertion into a sheath or equivalent mechanism of a delivery catheter. Once inside the body, the prosthetic valve 110 can be advanced from the delivery sheath, which allows the prosthetic valve to expand to its functional size.

Suitable plastically-expandable materials that can be used to form the frame 112 include, without limitation, stainless steel, a biocompatible, high-strength alloys (e.g., a cobalt-chromium or a nickel-cobalt-chromium alloys), polymers, or combinations thereof. In particular embodiments, the frame 112 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. It has been found that the use of MP35N® alloy to form frame 112 provides superior structural results over stainless steel. In particular, when MP35N® alloy is used as the frame material, less material is needed to achieve the same or better performance in radial and crush force resistance, fatigue resistance, and corrosion resistance. Moreover, since less material is required, the crimped profile of the frame can be reduced, thereby providing a lower profile prosthetic valve assembly for percutaneous delivery to the treatment location in the body.

The frame 112 in the illustrated embodiment comprises a first, lower row I of angled struts 128 arranged end-to-end and extending circumferentially at the inflow end 115 of the frame; a second row II of circumferentially extending, angled struts 130; a third row III of circumferentially extending, angled struts 132; a fourth row IV of circumferentially-extending, angled struts 134; and a fifth row V of circumferentially-extending, angled struts 136 at the outflow end 119 of the frame. A plurality of substantially straight axially-extending struts 138 can be used to interconnect the struts 128 of the first row I with the struts 130 of the second row II. The fifth row V of angled struts 136 are connected to the fourth row IV of angled struts 134 by a plurality of axially-extending window frame portions 140 (which define the commissure windows 126) and a plurality of axially-extending struts 142. Each axial strut 142 and each frame portion 140 extends from a location defined by the convergence of the lower ends of two angled struts 136 to another location defined by the convergence of the upper ends of two angled struts 134.

Each commissure window frame portion 140 mounts a respective commissure of the leaflet structure 114. As can be seen, each frame portion 140 is secured at its upper and lower ends to the adjacent rows of struts to provide a robust configuration that enhances fatigue resistance under cyclic loading of the prosthetic valve compared to known, cantilevered struts for supporting the commissures of the leaflet structure. This configuration enables a reduction in the frame wall thickness to achieve a smaller crimped diameter of the prosthetic valve. In particular embodiments, the thickness of the frame 112 measured between the inner diameter and outer diameter is about 0.48 mm or less.

The struts and frame portions of the frame 112 collectively define a plurality of open cells of the frame. At the inflow end 115 of the frame 112, struts 128, struts 130, and axial struts 138 define a lower row of cells defining openings 144. The second, third, and fourth rows of struts 130, 132, and 134 define two intermediate rows of cells defining openings 146. The fourth and fifth rows of struts 134 and 136, along with frame portions 140 and struts 142, define an upper row of cells defining openings 148. The openings 148 are relatively large and are sized to allow portions of the leaflet structure 114 to protrude, or bulge, into and/or through the openings 148 when the frame 112 is crimped in order to minimize the crimping profile.

The main functions of the inner skirt 116 are to assist in securing the valvular structure 114 to the frame 112 and to assist in forming a good seal between the prosthetic valve 110 and the native annulus by blocking the flow of blood through the open cells of the frame 112 below the lower edge of the leaflets 122. The inner skirt 116 desirably comprises a tough, tear resistant material such as polyethylene terephthalate (PET), although various other synthetic or natural materials can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 116 can have a variable thickness, for example, the skirt can be thicker at least at one of its edges than at its center. In one implementation, the skirt 116 can comprise a PET skirt having a thickness of about 0.07 mm at its edges and about 0.06 mm at its center. The thinner skirt can provide for better crimping performance while still providing good perivalvular sealing.

The skirt 116 can be secured to the inside of frame 112 via sutures 150. Valvular structure 114 can be attached to the skirt 116 via one or more reinforcing strips (not shown, which collectively can form a sleeve), for example thin, PET reinforcing strips, discussed below, which enable secure suturing and protect the pericardial tissue of the leaflet structure from tears. Valvular structure 114 can be sandwiched between the skirt 116 and the thin PET strips. Sutures 124, which secure the PET strip and the leaflet structure 114 to the skirt 116, can be any suitable suture, such as Ethibond Excel® PET suture (Johnson & Johnson, New Brunswick, New Jersey). Sutures 124 desirably track the curvature of the bottom edge of leaflet structure 114.

The outer skirt 118 can be laser cut or otherwise formed from a strong, durable piece of material. The outer skirt 118 can have a substantially straight lower edge and an upper edge 162 defining a plurality of alternating projections 164 and notches 166, or castellations. The lower edge of the skirt 118 can be sutured to the lower edge of the inner skirt 116 at the inflow end 115 of the prosthetic valve 110. Each projection 164 can be sutured to the second rung II of struts 130 of the frame 112.

As can be seen in FIG. 1, the outer skirt 118 is secured to the frame 112 such that when the frame is in its expanded configuration (e.g., when deployed in a subject), there is excess material between the lower edge of the skirt and the upper edge 162 that does not lie flat against the outer surface of the frame 112. The outer skirt 118 can be secured directly to the frame 112 and/or indirectly to the frame, for example, by securing the outer skirt to the inner skirt 116, which is directly secured to the frame 112. In the expanded configuration of the prosthetic valve 110, the distance between the upper and lower attachment points of the outer skirt 118 decreases (foreshortens), resulting in outward radial buckling of the outer skirt 118. Additionally, the excess material between the lower and upper edges of the outer skirt 118 allows the frame 112 to elongate axially when crimped without any resistance from the outer skirt. In some embodiments, the outer skirt 118 includes an axial length that can be substantially the same as the axial length between the upper and lower attachment points of the outer skirt to the frame 112 when the frame is fully crimped. In such embodiments, when the frame 112 is fully crimped, the outer skirt 118 can lie flat against the outer surface of the frame.

The leaflets 122 can be further secured to the frame 112 by commissure bars (analogous to the commissure bars 224 of FIG. 2A) positioned on the inner surface of the leaflets 122 adjacent the commissure windows 126. In specific examples, the commissure bars can be made of metal and can include apertures which can be used to suture the commissure bars to the leaflets 122 and the frame 112. Commissure bars suitable for use in the present disclosure, in addition to a prosthetic valve with which a disclosed crimping accessory device may be used, are disclosed in U.S. Pat. No. 7,993,394, incorporated by reference herein.

The prosthetic valve 110 can be fabricated in the form shown in FIG. 1, and then crimped to a smaller diameter prior to implantation in a patient. Once the crimped, or compressed, prosthetic valve 110 is proximate the implantation site, it can be expanded to its original form. It can be desirable that after expansion from a crimped state that the prosthetic valve 110 is in at least substantially the same form as before the prosthetic valve was crimped. For example, it can be desirable that the leaflets 122 not be damaged or deformed during the crimping process and subsequent expansion.

Further details regarding the prosthetic valve 110 are disclosed in U.S. Patent Publication 2015/0320556, incorporated by reference herein. However, embodiments of the disclosed crimping accessory device are not limited to use with any particular type of prosthetic valve.

FIG. 2A illustrates the outflow end of a prosthetic valve 210 having leaflets 214 of a leaflet assembly 212 in a desired configuration when the valve is returned to an expanded state after having been previously crimped to a smaller diameter. FIG. 2B illustrates the outflow end of the prosthetic valve 210 when the leaflets 214 have been crimped in a manner that produces asymmetry in the leaflets after the valve is returned to an expanded state after previously being crimped to a smaller diameter. In at least some aspects, the prosthetic valve 210 can be, or can be configured similar to, the prosthetic valve 110 of FIG. 1.

With reference first to FIG. 2A, the leaflet assembly 212 can be coupled to a frame 216. Commissures of the leaflets 214 can be symmetrically disposed in the leaflet assembly 212 circumferentially about the frame 216. For example, each commissure can include radially-inwardly extending portions 218 of overlapping leaflet material. These portions 218 can be radially and axially aligned. Each commissure can further include laterally-extending portions 222 of overlapping leaflet material. These portions 222 can be axially and circumferentially aligned.

Support bars 224 can be secured, such as by suturing, against the interior (radially inner) surfaces 226 of the leaflets 214, such as at the intersection of the radially-inwardly-extending portions 218 and the laterally-extending portions 222. The support bars 224 can apply a compressive force to the leaflets 214 to help secure them in position. Each member of a pair of support bars 224 proximate a commissure of a pair of leaflets 214 can be circumferentially, radially, and axially symmetric or aligned.

Maintaining the symmetric arrangement of the leaflets 214, including the commissures, support bars 224, radially-inwardly-extending portions 218, and laterally-extending portions 222, as the prosthetic valve 210 is crimped and expanded can be advantageous. For example, maintaining this arrangement can help reduce damage to the prosthetic valve 210, such as displacement of the support bars 224 or tearing of the material of the leaflets 214. In addition, maintaining the leaflets 214 in a symmetric relationship can improve the functioning of the prosthetic valve 210, such as by allowing the prosthetic valve to open to a larger degree, and close more securely, than if the leaflets were misaligned.

In FIG. 2B, the leaflets 214 are shown as having an asymmetric arrangement, with the leaflets 214 and other components of the prosthetic valve 210 having been moved out of alignment. Rather than having a concave appearance, as do the leaflets 214 in FIG. 2A, the leaflets of FIG. 2B have a pinwheel appearance. In addition, each support bar 224 of a pair of adjacent support bars can be radially, axially, or circumferentially offset from the other. Whereas lateral edges 240 of the support bars 224 are parallel to the radius of the prosthetic valve 210 in FIG. 2A, in FIG. 2B the support bars 224 have been twisted out of this position. Similarly, adjacent radially-inwardly-extending portions 218 are asymmetrically stretched and radially and circumferentially offset from one another, and, the laterally-extending portions 222 have been twisted out of circumferential alignment.

Figure 3A:
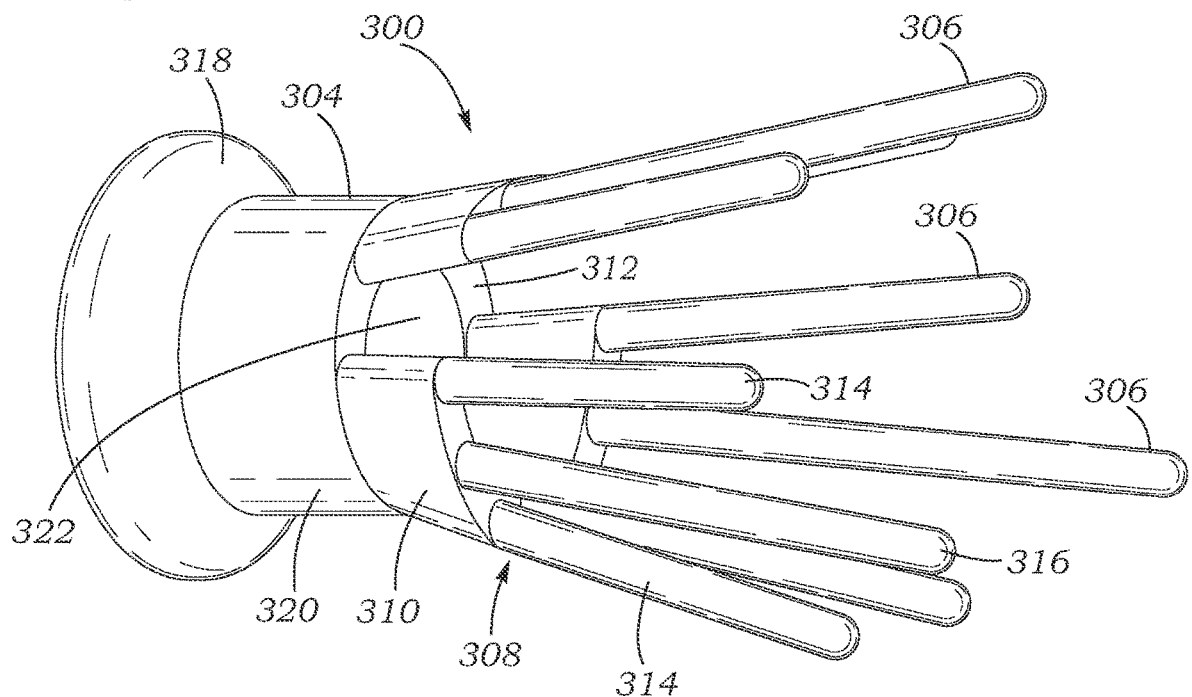
FIG. 3A is perspective view of an exemplary crimping accessory device having a plurality of axially-extending fingers.
Figure 3B:
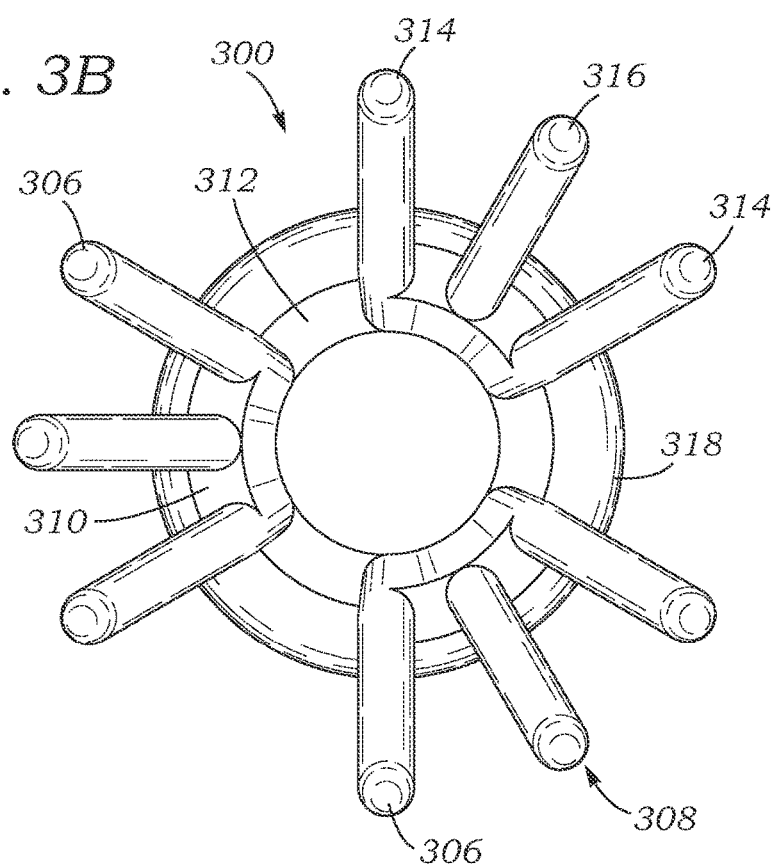
FIG. 3B is an elevational view from an axial end of the crimping accessory device of FIG. 3A.

FIGS. 3A and 3B illustrate an embodiment of a crimping accessory device or tool 300 that can be used to promote symmetric leaflet folding during the crimping process, as well as protecting the leaflets from damage from the metal struts of the frame, thereby providing atraumatic crimping of the prosthetic valve. The device 300 in the illustrated configuration comprises a handle in the form of an elongate shaft 304 and one or more shielding members, or fingers, 306 extending from the head 312 of the shaft 304.

In the illustrated embodiment, there are three sets 308 of fingers 306, each set corresponding to one leaflet of a prosthetic valve having three leaflets (as shown in FIG. 1). The fingers 306 in each set 308 can extend from an arcuate mount 310 axially-extending from the head 312 of the shaft 304. Each set 308 in the illustrated configuration includes three fingers 306, including two outer fingers 314 and one inner finger 316 located intermediate (circumferentially between) the outer fingers. In at least some cases, the inner fingers 316 can be longer than the outer fingers 314.

In alternative embodiments, the number of sets 308, as well as the number of fingers 306 in each set, can be greater or fewer than three. For example, in some cases, the numbers of sets 308 can depend upon the number of leaflets present in the prosthetic valve to be crimped. In alternative embodiments, each finger 306 or each set 308 can be connected to a separate shaft so that each finger or set of fingers and shaft function as a separate tool, and one or more of such tools can be used for crimping a prosthetic valve.

The fingers 306 can be sized and shaped (including the length, diameter, and cross-sectional shape) to be placed in the space between each leaflet and the frame of a prosthetic valve (e.g., the leaflets 122 and the frame 112 of the prosthetic valve 110 of FIG. 1), and shield the leaflets from coming into direct contact with the metal struts of the frame as the diameter of the frame is reduced during the crimping process. In particular examples, one or more of the fingers 306 can have a circular, semi-circular, or elliptical cross-sectional shape. The shape of the fingers 306 can vary, such as along the length of a finger. In some cases, the cross-sectional shape can be different at different axial points on the finger 306. The diameter of the fingers 306 can also vary along their length, including fingers having larger diameters at their proximal and distal ends, and a reduced diameter at a medial portion of the fingers. Or, the diameter of a finger 306 can taper along all or potion of the length of the finger. In further aspects, the fingers 306 can have constant shape and dimensions along their length.

In some embodiments, the fingers 306 are sized, shaped, and spaced apart from one another such that each set 308 of fingers can be associated with a particular leaflet. Typically, the spaces between the outer surface of each leaflet and the inner surface of the frame are separated by the commissures of a leaflet assembly (e.g., the valve structure 114 of FIG. 1), which form vertical seams extending from the coaptation edges of the leaflets at the inner surface of the frame. It is therefore desirable to have at least one finger for each leaflet of the prosthetic valve so that at least one finger can be easily placed behind each leaflet.

As best shown in FIG. 3B, the circumferential spacing or distance between each set 308 of fingers 306 can be larger than the circumferential spacing or distance between the fingers 306 in each set, including the spacing or distance between the inner finger 316 and the outer fingers 314 in a set. The larger circumferential spacing between the sets 308 can help accommodate the commissures of the leaflets. The circumferential spacing between the sets 308, and between the fingers 306 in a set, can be varied as needed to accommodate the leaflet structure, including the commissures, and to promote a desired leaflet folding pattern.

The fingers 306 can be configured such that one or more of the fingers in a set 308 can be disposed between the outer surface of the leaflet and the inner surface of the frame, and one or more of the fingers in the set can abut the inner leaflet surface. In some cases, the fingers 306 can be made from a sufficiently resilient material such that the fingers can be bent radially inwardly or outwardly to facilitate positioning the fingers against the inner or outer surfaces of the leaflets. In further cases, the fingers 306 may be disposed at different angles relative to the longitudinal axis of the device 300. For example, fingers 306 to be placed against the inner leaflet surface (e.g., outer fingers 314) can extend from the shaft 304 at a smaller angle relative to the axis of the device 300 than fingers to be placed between the outer leaflet surface and the frame (e.g., inner fingers 316).

The fingers 306 desirably comprise a soft, flexible, resilient, lubricious and/or compressible material, including, but not limited to, natural or synthetic sponge (e.g., polyurethane sponge), a foamed material made of a suitable polymer such as polyurethane or polyethylene, any of various suitable elastomeric materials, such as polyurethane, silicone, polyolefins, polytetrafluoroethylene (PTFE), or a variety of hydrogels, any of various types of natural tissue, such as fixed pericardial tissue, to name a few. In other embodiments, the fingers 306 can comprise inflatable structures (similar to the inflatable balloon of a balloon catheter) that can be inflated with a fluid (a gas or a liquid) prior to use. In other embodiments, the fingers 306 can be made from a different material, including rigid materials.

The shaft 304 can have a base portion 318. The base portion 318 can be flared, having a larger diameter than a body 320 of the shaft 304. The larger diameter of the base portion 318 can allow the base portion to act as a handle for the device 300. For example, the base portion 318 may facilitate inserting the device 300 into, and removing it from, a prosthetic valve.

The shaft 304 can be hollow, defining a lumen 322. The lumen 322 can have a diameter sufficiently large to allow passage of components to be used in implanting, or crimping, a prosthetic valve. For example, the lumen 322 may be sufficiently large to allow passage of a catheter used to deliver the prosthetic valve to a patient, or a balloon or other expansion or deployment mechanism. In other embodiments, the shaft 304 can be solid or have a smaller lumen 322.

Figure 4:
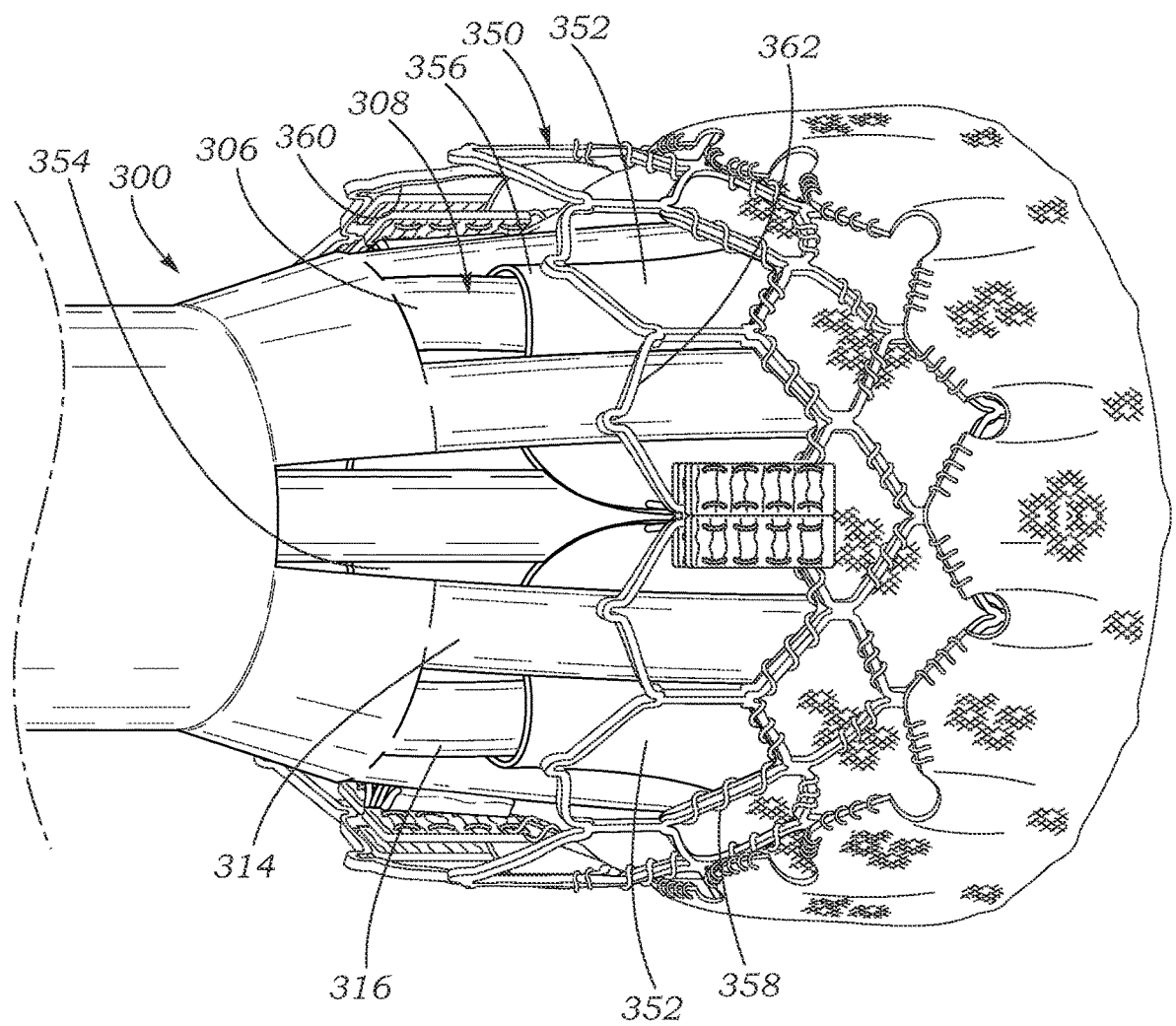
FIG. 4 is a perspective view of the crimping accessory device of FIG. 3 in use with a prosthetic valve.

The device 300 can be used when crimping a plastically-expandable or self-expandable prosthetic valve. FIG. 4 illustrates the device 300 in use with a prosthetic valve 350, which can be, for example, the prosthetic valve 110 of FIG. 1, or the prosthetic valve 210 of FIG. 2A. The prosthetic valve 350 can include a plurality of leaflets 352, each having an inner surface 354 and an outer surface 356. The leaflets 352 can be coupled to a frame 358, the frame having an inner surface 360 and an outer surface 362.

For each of the sets 308 of fingers 306, the outer fingers 314 of the set can be disposed between the outer leaflet surface 356 and the inner surface 360 of the frame 358. The inner finger 316 of each set 308 abuts the inner surface 354 of a leaflet 352. During insertion of the device 300 into the prosthetic valve 350, the inner fingers 316 can be deflected radially inwardly. The radial-outward bias of the inner fingers 316 can cause the inner fingers 316 to exert a radially-outwardly-directed force against the inner surface 354 of a leaflet 352, which can help secure the device 300 to the valve 350, and maintain the position of the fingers 306 relative to the leaflets as the valve and device are crimped.

Securing the leaflets 352 between the inner 316 and outer fingers 314 can help prevent the leaflets from contacting the frame 358, and possibly becoming damaged, during the crimping process. In addition, securing the leaflets 352 in this manner can help maintain the position of the leaflets during crimping, which can aid the leaflets in folding in a symmetrical manner. Symmetrical folding can also reduce the potential for damage to the prosthetic valve 350, and potentially improve its operation compared to a valve where the leaflets 352 folded asymmetrically.

Figure 5:
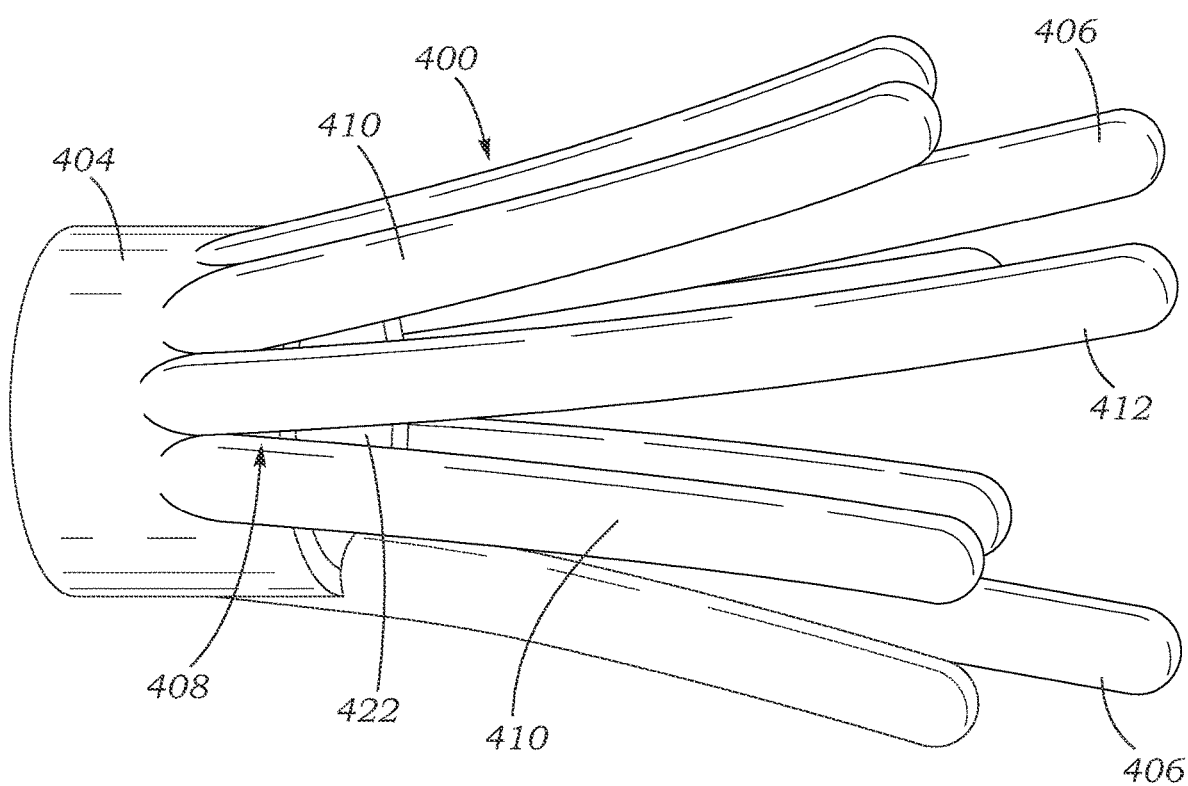
FIG. 5 is perspective view of an exemplary crimping accessory device having a plurality of axially-extending fingers.

FIG. 5 illustrates an alternative embodiment of a crimping accessory device or tool 400. The device 400 in the illustrated configuration can comprise a handle in the form of an elongate shaft 404 and one or more shielding members, or fingers, 406 extending axially from the radial surface of the shaft 404. As with the device 300, the fingers 406 of the device 400 can be disposed in sets 408, with each set to be associated with a leaflet of a prosthetic valve. Each set 408 can include outer fingers 410 and one or more inner fingers 412 intermediate the outer fingers. In some implementations, the inner fingers 412 can be longer than the outer fingers 410. The fingers 406 can be configured in a similar manner to the fingers 306 of the device 300. Compared with the fingers 306, the fingers 406 can have a larger diameter or width and/or a flatter cross-sectional shape.

The shaft 404 can be hollow, defining a lumen 422. The lumen 422 can have a diameter sufficiently large to allow passage of components to be used in implanting, or crimping, a prosthetic valve. For example, the lumen 422 may be sufficiently large to allow passage of a catheter used to deliver the prosthetic valve to a patient, or a balloon or other expansion or deployment mechanism. In other embodiments, the shaft 404 can be solid or have a smaller lumen 422.

In the device 400, each of the fingers 406 extends from the shaft 404 at the same angle relative to the axis of the shaft. In this embodiment, the fingers 406 can be made from a resilient material (e.g., a material described for the fingers 306 of FIG. 3) such that the fingers 406 can be bent to facilitate their placement against the inner or outer surfaces of a leaflet. The device 400 is shown with three sets 408 of fingers 406, such as for use with a prosthetic valve having three leaflets. In alternative embodiments, the number sets 408, as well as the number of fingers 406 in each set, can be greater or fewer than three. In addition, the fingers 406 may extend from the shaft 404 at different angles.

Figure 6:
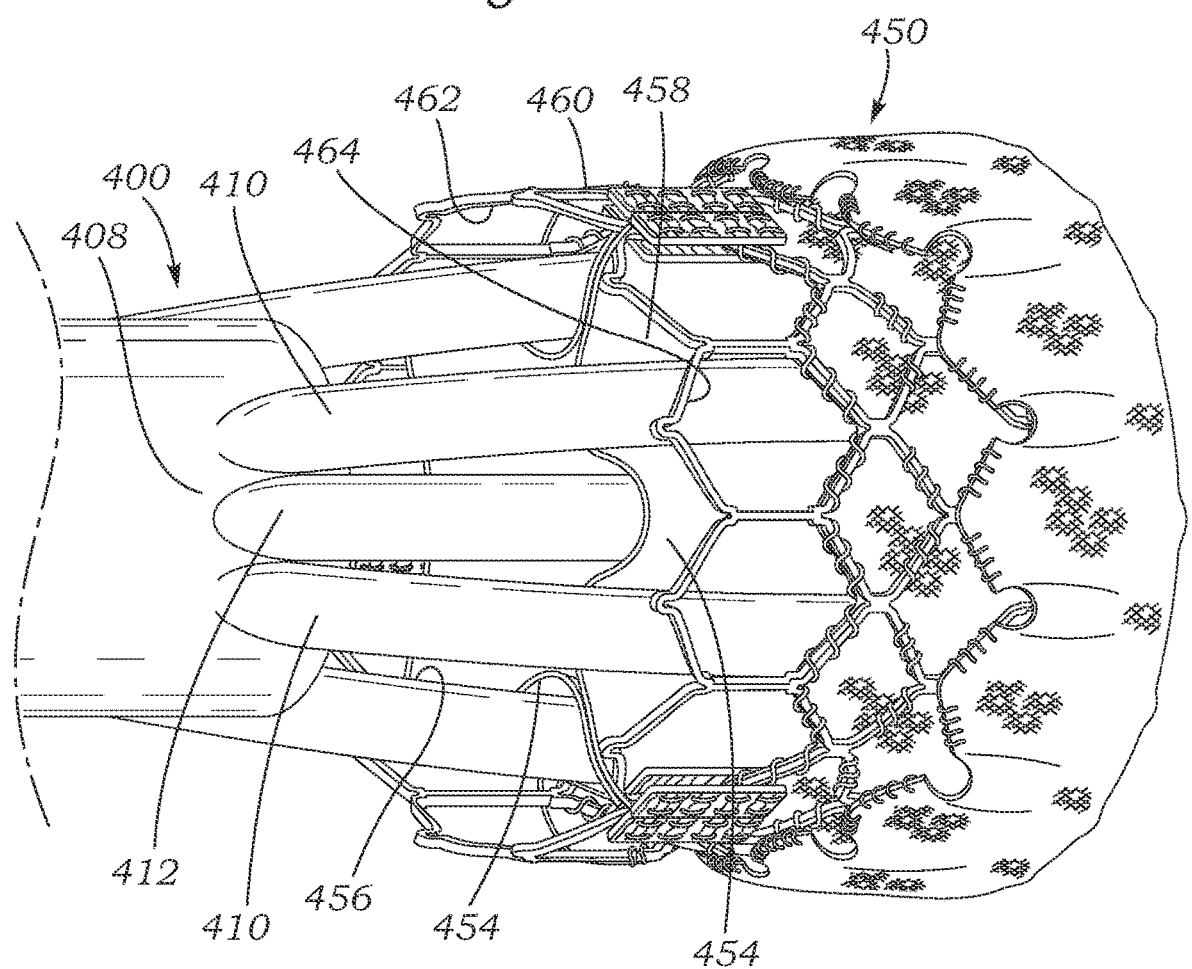
FIG. 6 is a perspective view of the crimping accessory device of FIG. 5 in use with a prosthetic valve.

FIG. 6 illustrates the device 400 in use with a prosthetic valve 450. The prosthetic valve 450 includes three leaflets 454, each having an inner surface 456 and an outer surface 458. The leaflets 454 are disposed circumferentially about a frame 460. The frame 460 has an inner surface 462 and an outer surface 464.

Outer fingers 410 of each set 408 can be disposed between the outer leaflet surface 458 and the inner surface 462 of the frame 460. An inner finger 412 of each set 408 can abut the inner leaflet surface 456. The inner finger 412, having been deflected radially-inwardly during insertion of the device 400 into the valve 450, can be biased radially-outwardly, such that it exerts a radially-outwardly-directed force again the inner leaflet surface 456. This force can help secure the device 400 to the valve 450, and help maintain the position of the fingers 406 relative to the leaflets 454 as the device and the valve are crimped.

As with the device 300, using the device 400 to secure the leaflets 454 between the inner 412 and outer fingers 410 can help prevent the leaflets from contacting the frame 460, and possibly becoming damaged, during the crimping process. In addition, securing the leaflets 454 in this manner can help maintain the position of the leaflets during crimping, which can aid the leaflets in folding in a symmetrical manner. Symmetrical folding can reduce the potential of damage to the prosthetic valve 450, and potentially improve its operation compared to a valve where the leaflets 454 folded asymmetrically.

Figure 7:
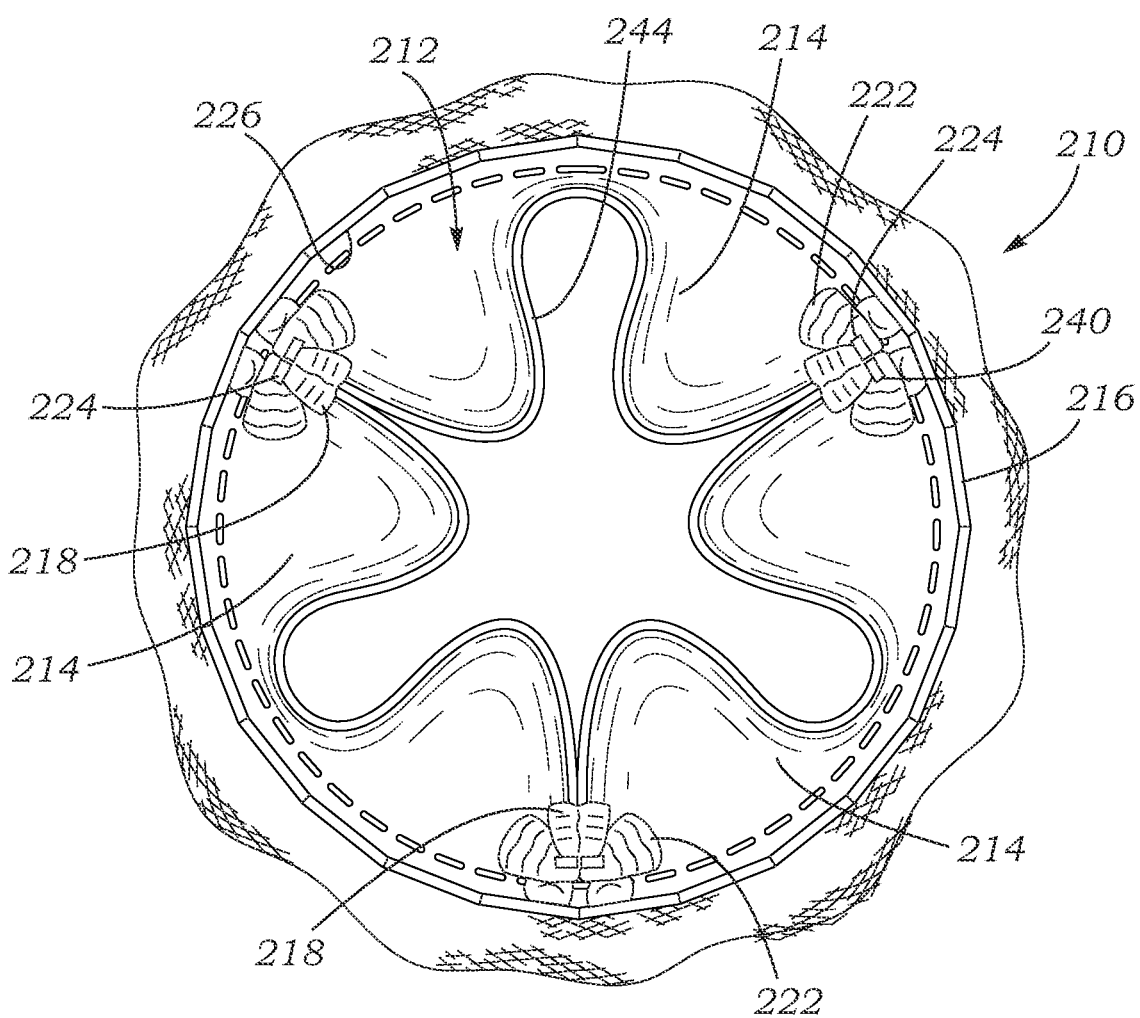
FIG. 7 is a plan view of the outflow end of a partially crimped prosthetic valve, showing the valve leaflets arranged symmetrically about the circumference of the valve frame.

FIG. 7 illustrates the outflow end of the prosthetic valve 210 of FIG. 2A partially crimped using a crimping accessory device or tool of the present disclosure, such as the device 300 or the device 400. The free edges 244 of the leaflets 214 exhibit a symmetric, "accordion" folding pattern, where the edges are symmetrically scalloped. Despite having been partially crimped, the alignment/symmetry of radially-inwardly-extending portions 218, the laterally-extending portions 222, and the commissure bars 224 have been maintained.

FIG. 8 illustrates an alternative embodiment of a crimping accessory device or tool 500. The device 500 in the illustrated configuration comprises a handle in the form of an elongate shaft 504 and one or more shielding members, or fingers, 508 extending axially from the head 510 of the shaft 504. The shaft 504 can be hollow, defining a lumen 512.

As shown, the device 500 includes three fingers 508. However, the device 500 can include more or fewer fingers 508. In particular examples, the number of fingers 508 can correspond to a number of leaflets associated with a prosthetic valve with which the device 500 will be used. In further examples, the device 500 can include more than one finger 508 for a leaflet. When more than one finger 508 is included for each leaflet, the fingers can be organized in sets. The fingers 508 can be configured to be disposed between an outer surface of the leaflet and an inner surface of a frame of a prosthetic valve. However, particularly when the device 500 incudes multiple fingers 508 for each leaflet, at least a portion of the fingers can abut the inner leaflet surface, such as described above for devices 300 and 400.

Each of the fingers 508 can have a retaining member or hook 514 disposed on its exterior surface. The hooks 514 can define notches 516, or axial openings directed toward axial tips 520 of the fingers 508. The hooks 514 can be used to appropriately position the device 500 relative to a prosthetic valve. For example, the hooks 514 can be configured to abut portions of the frame of the prosthetic valve when appropriately positioned. In this way, the fingers 508 can be advanced toward the prosthetic valve until the hooks 514 engage the frame. Once the frame is engaged, the hooks 514 can resist further axial movement of the device 500. Thus, the hooks 514 can help ensure that the device 500 is advanced far enough within the prosthetic valve that the fingers 508 can protect the leaflets during crimping, and to help secure the device 500 to the prosthetic valve, but resist excessive axial movement which might cause the fingers 508 to puncture the leaflets or otherwise damage the prosthetic valve.

FIG. 9 illustrates the device 500 in use with a prosthetic valve 550. The prosthetic valve 550 includes three leaflets 554, each having an inner surface 556 and an outer surface 558. The leaflets 554 are disposed circumferentially about a frame 560. The frame 560 has an inner surface 562 and an outer surface 564.

Each finger 508 of the device 500 is disposed between the outer surface 558 of a leaflet 554 and the inner surface 562 of the frame 560 of the prosthetic valve 550. Each hook 514 can engage a portion of the frame 560 formed by two intersecting frame struts 566. A line of suture 568 can help secure the device 500 to the prosthetic valve 550, such as extending between openings in the frame 560 formed by the frame struts 566. The suture 568 can extend about the fingers 508 (radially inwardly, as shown, but in other implementations the suture can extend radially inwardly and radially outwardly adjacent and about the fingers 508).

A delivery device 570, which can include a shaft 572 coupled to a nosecone 574, and an inflatable balloon 578 mounted on the shaft, with a stylus 576 inserted axially through a lumen of the nosecone and a lumen of the shaft, can be inserted through the lumen 512 of the shaft 504. Prior to crimping, the balloon 578 can be centered within the prosthetic valve 550. The stylus 576 can be used, for example, to protect against kinking of the shaft 572 during crimping, packaging, and storage of the prosthetic valve 550 and the delivery device 570. Prior to use, the stylus 576 can be discarded. During implantation, the delivery device 570 can be advanced over a guidewire, as known in the art.

Inserting the delivery device 570 through the lumen 512 of the device 500 can facilitate insertion of the delivery device into the prosthetic valve 550 by serving as a guide, which can also help prevent the prosthetic valve from being damaged while it is being mounted on the delivery device.

Figure 10:
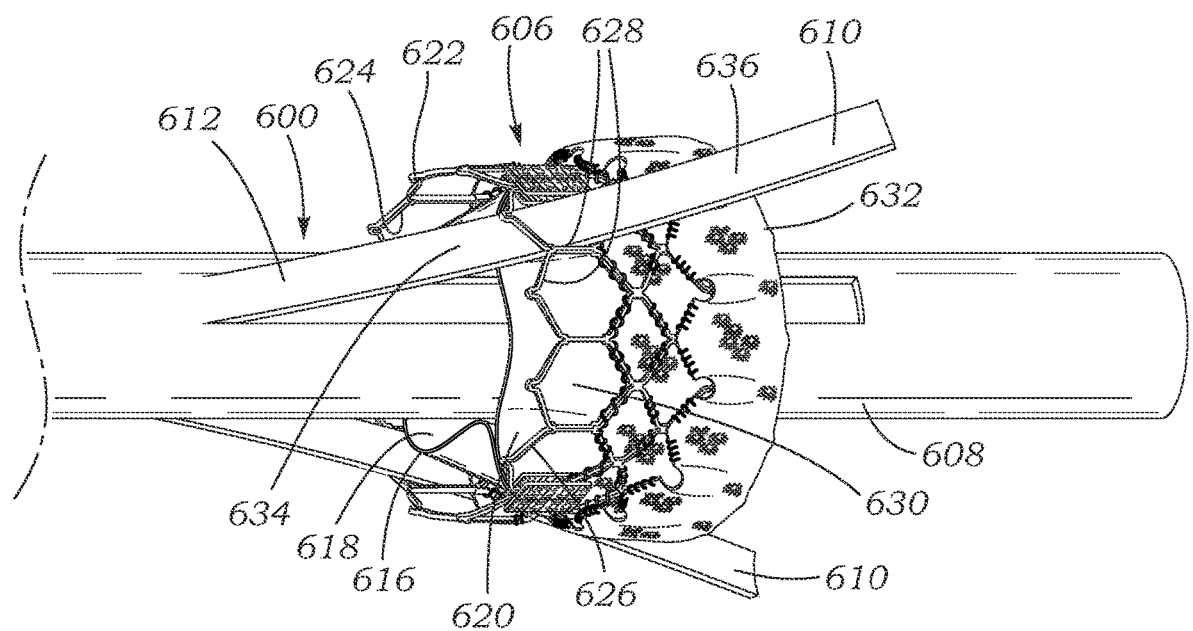
FIG. 10 is a perspective view an exemplary crimping accessory device in use with a prosthetic valve, where at least one finger of the crimping accessory device extends through a window in the frame of the prosthetic valve.

FIG. 10 illustrates a further embodiment of a crimping accessory tool or device 600 in use with a prosthetic valve 606. The device 600 includes an elongate shaft 608. One or more shielding members, or fingers, 610 can extend axially from the radial surface of the shaft 608. In particular examples, the fingers 610 can be formed from the material of the shaft 608. For example, the fingers 610 can be formed by cutting a portion of the radial surface of the shaft 608 such that the cutout section forming each finger remains attached to the shaft at its proximal end 612. The fingers 610 thus extend in a cantilevered manner from the shaft 608.

The prosthetic valve 606 can include a plurality of leaflets 616, each having an inner surface 618 and an outer surface 620. The leaflets 616 can be coupled to a rigid frame 622 having an inner surface 624 and an outer surface 626. The frame 622 can be formed from a plurality of struts 628, such as metal struts. The struts 628 can form a plurality of windows 630.

The fingers 610 can extend toward the distal or outflow end 632 of the prosthetic valve 606. A medial portion 634 of each finger 610 can extend between the outer surface 620 of the leaflets 616 and the inner surface 624 of the frame 622. A distal portion 636 of each finger 610 can pass radially outwardly through one of the frame windows 630 and extend radially outwardly from the prosthetic valve 606.

The fingers 610 can prevent at least a portion of the leaflets 616 from contacting the frame 622, thereby avoiding damage to the leaflets. The fingers 610 can then be removed from the prosthetic valve 606 by simply pulling the device 600 in the axial direction away from the prosthetic valve 606.

In one advantageous feature, crimping accessory devices disclosed herein may be formed of a polymeric material to reduce cost and weight. In addition, due to the efficiency of the construction, the crimping accessory devices may be manufactured at a relatively low cost. Accordingly, the crimping accessory devices described herein are well-suited for single-use purposes, thus obviating the need for sterilization between uses.

In some cases, the disclosed crimping accessory devices (e.g., the devices 300, 400, 500, or 600) can be maintained at a desired position with respect to a prosthetic valve to be crimped by manually ensuring that the crimping accessory device and the prosthetic valve are moved as a unit (i.e., grasping the crimping accessory device and the prosthetic valve and holding them together during the crimping process). In other cases, compressive or frictional forces between the crimping accessory device and the prosthetic valve, such as from the leaflets or frame, can help secure the crimping accessory device at a desired position with respect to the prosthetic valve. In some aspects, additional securing means can be used to secure the crimping accessory device to a prosthetic valve to be crimped.

In a particular implementation, one or more lines of suture can be threaded between the fingers of the crimping accessory device and one or more portions of the prosthetic valve. For instance, one or more sutures can be threaded through or around the fingers of a crimping accessory device and through openings in a frame of the prosthetic valve. Sutures used in attaching the crimping accessory device to the prosthetic valve can be threaded through the axial opening between the fingers of the crimping accessory device, and/or through a shaft of the crimping accessory device.

Once the prosthetic valve has been crimped in association with the crimping accessory device to a desired degree, the sutures can be manually cut or severed with a cutting device associated with the prosthetic valve or crimping accessory device. In a particular example, the crimping accessory device can have a pull-tab cutting component that severs the sutures when pulled axially toward the shaft of the crimping accessory device.

Securing the crimping accessory device to the prosthetic valve may be particularly advantageous when the prosthetic valve is partially crimped at a first time or location and final crimping will be performed at a second time or location. For example, the prosthetic valve may be partially crimped during manufacturing, and the prosthetic valve and crimping accessory device shipped as an assembly to a medical provider. When the prosthetic valve is to be implanted, the medical provider can remove the crimping accessory device from the prosthetic valve (such as by severing retaining sutures), crimp the prosthetic valve to the final desired diameter, and then implant the prosthetic valve in a patient.

Figure 11:
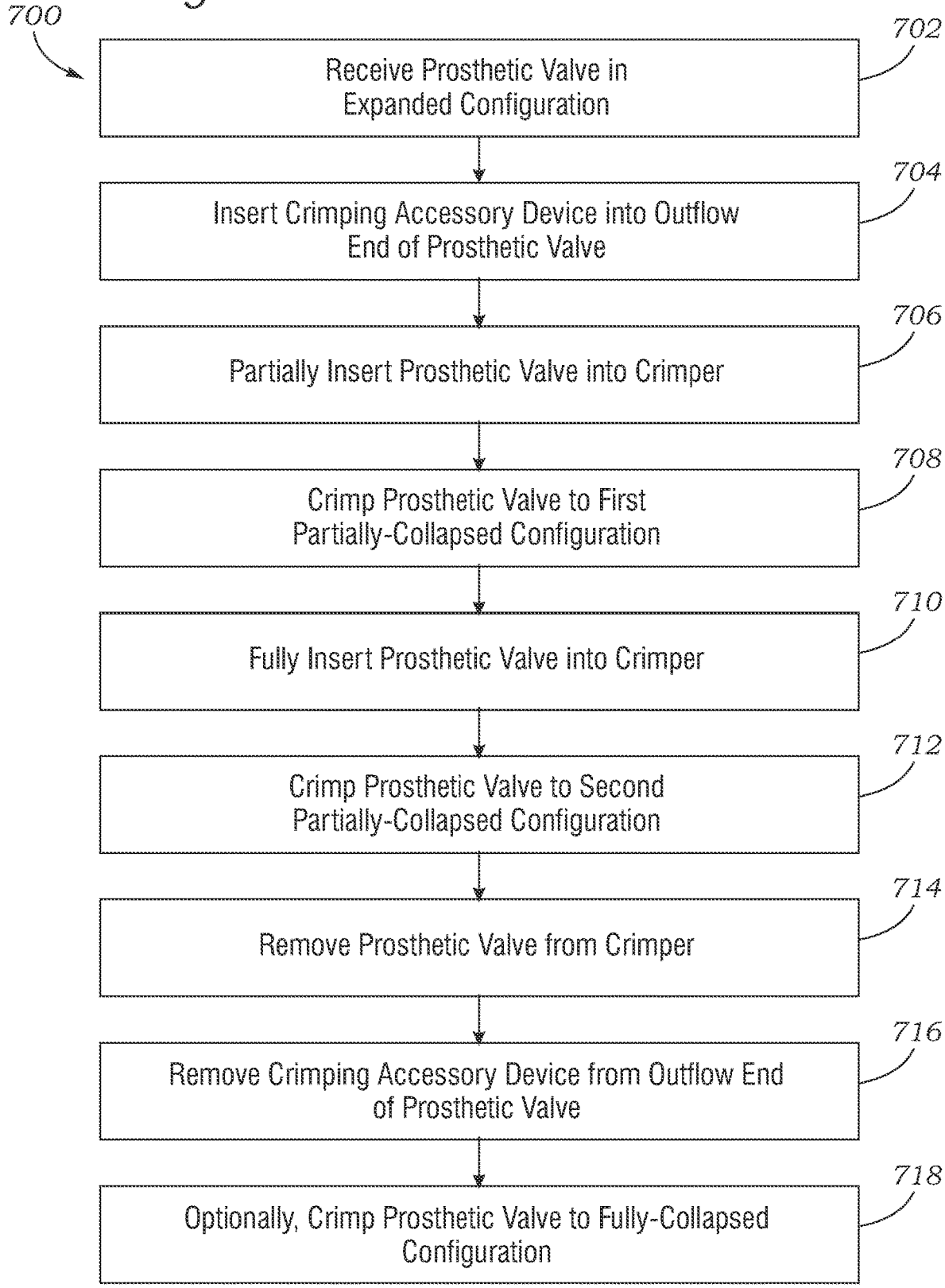
FIG. 11 illustrates a process for crimping an expandable and collapsible prosthetic valve in cooperation with a crimping accessory device.

FIG. 11 illustrates a multi-step process 700 for crimping an expandable and collapsible prosthetic valve (such as valve 110), comprising an outflow end portion and an inflow end portion, in cooperation with a crimping accessory device having a plurality of axially-extending fingers, such as any of the embodiments of a crimping accessory device disclosed herein. By using the multi-step process 700, the prosthetic valve can be crimped to a small diameter while reducing or eliminating damage to the valve leaflets through contact with a metal frame of the prosthetic valve and, in at least some cases, symmetric leaflet folding can be encouraged. In particular examples, the process 700 can be carried out using the crimping device disclosed in U.S. Patent Publication 2015/0336150, incorporated by reference herein. In further examples, a different crimping device or means can be used to crimp a prosthetic valve in cooperation with a disclosed crimping accessory device.

Using the multi-step process 700, the prosthetic valve can be crimped to a small profile, suited for delivery through a patient's vasculature on the distal end of a delivery device. In some cases, the prosthetic valve can be crimped to a partially collapsed profile for delivery to a health care provider for further crimping prior to implantation in a recipient. The prosthetic valve can be crimped directly onto a delivery device (e.g., onto the balloon of a balloon catheter or onto a shaft of a balloon catheter adjacent the balloon). Once crimped (partially or fully), the prosthetic valve can be packaged in a sterile package alone or along with the delivery catheter and then delivered to a health care provider. The prosthetic valve and the delivery catheter can be stored until needed for a procedure, at which point the physician can remove the prosthetic valve and the delivery catheter from the package and then implant the prosthetic valve in a patient. In alternative embodiments, the prosthetic valve can be provided to health care providers in a fully expanded state. Process 700 can be used by the end user to crimp the prosthetic valve on a delivery apparatus just prior to implantation.

As shown in FIG. 11, at process block 702 the process 700 begins by receiving an expandable prosthetic valve in a fully expanded configuration. At process block 704, a crimping accessory device is inserted into the outflow end of the prosthetic valve, with at least one finger of the crimping accessory device being disposed between an inner surface of the frame and an outer surface of a valve leaflet. The crimping process can continue by at least partially inserting the expanded prosthetic valve into a valve crimper at process block 706. The inflow end portion of the prosthetic valve can be inserted into the crimping device in a position where the jaws of the crimper device can contact the inflow end of the frame of the prosthetic valve. In other embodiments, the entire prosthetic valve can be inserted into the crimper at process block 706.

At process block 708, the prosthetic valve can be crimped to a first partially-collapsed configuration. In some embodiments, an expandable prosthetic valve can be considered crimped to the first partially-collapsed configuration, and process block 708 can accordingly be considered complete, when the prosthetic valve has a diameter that is about 60% or about 50% (such as between about 40% and about 60%) of the diameter of the prosthetic valve in the fully expanded configuration. In more particular embodiments, an expandable prosthetic valve can be considered crimped to the first partially-collapsed configuration, and process block 708 can accordingly be considered complete, when the valve outside diameter is between about 15 mm and about 20 mm at the outflow end, and between about 15 mm and about 26 mm at the inflow end. In other examples, process block 708 can be considered complete when the prosthetic valve has been radially compressed by a different amount.

At process block 710, the prosthetic valve can be fully inserted into the crimping jaws. The crimping process can continue at process block 712 by crimping the expandable prosthetic valve to a second partially-collapsed configuration. In some embodiments, the expandable prosthetic valve can be considered crimped to the second partially-collapsed configuration, and process block 712 can accordingly be considered complete, when the prosthetic valve has a diameter that is about 40% or about 30% (such as no more than about 40%, or between about 30% and about 40%) of the diameter of the prosthetic valve in the fully expanded configuration. In other examples, process block 712 can be considered complete when the prosthetic valve has been radially compressed by a different amount.

The crimping process can continue by removing the prosthetic valve from the crimper at process block 714. At process block 716, the crimping accessory device can be removed from the outflow end of the prosthetic valve.

The crimping process can optionally continue at process block 718 by crimping the expandable prosthetic valve to a fully collapsed configuration. At any step prior to process block 718, a delivery device can be inserted through the crimping accessory device and the prosthetic valve. For example, in cases where the prosthetic valve comprises a plastically-expandable frame, a balloon of the delivery device can be centered within the prosthetic valve for crimping the valve on the balloon. In some embodiments, the expandable prosthetic valve can be considered crimped to the fully-collapsed configuration, and process block 718 can accordingly be considered complete, when the diameter of the frame of the prosthetic valve is no more than about 5 mm. In additional embodiments the frame of the prosthetic valve has a diameter of no more than about 14 Fr in the fully crimped configuration. In one non-limiting example, the frame of a 26-mm prosthetic valve, when fully crimped, has a diameter of no more than about 14 Fr.

At the completion of any of the process blocks 702, 704, 706, 708, 710, 712, 714, and/or 716, the process can be paused for any appropriate period of time. That is, a succeeding process block need not begin immediately upon termination of a preceding process block.

In various embodiments, the prosthetic valve can be removed from the crimper at the completion of steps 708, 712, or 716, and then packaged in a sterile package for storage and/or delivery to a health care provider, with the remaining steps of the process 700 to be completed by the end user. In particular embodiments, the crimped or partially crimped prosthetic valve is packaged in a dry state. In alternative embodiments, the crimped or partially crimped prosthetic valve is packaged in a "wet" state within a container containing a preserving solution.

Although process 700 includes three crimping steps 708, 712, 718, in further examples, the process 700 can include more or fewer crimping steps. The crimping accessory device functions to promote symmetrical folding of the leaflets during the initial crimping stages. After removing the crimping accessory device, the leaflets will continue to fold in the desired manner as the valve is further crimped.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment, or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An assembly comprising:
   a prosthetic valve comprising a radially expandable and compressible annular frame, the annular frame having an outer surface and an inner surface, and a leaflet assembly supported inside the annular frame, the leaflet assembly comprising a plurality of leaflets, respective leaflets of the plurality of leaflets having an inner surface and an outer surface; and
   a crimping accessory device comprising a shaft and a plurality of axially-extending fingers fixedly secured to an end of the shaft and interposed between the inner surface of the frame and an outer surface of a first leaflet of the plurality of leaflets such that:
   (1) along a defined radial distance from an axis extending through the shaft of the crimping accessory device, an inner surface of a first axially-extending finger of the plurality of axially-extending figures is adjacent the outer surface of the first leaflet and an opposing outer surface of the first axially-extending finger is adjacent the inner surface of the frame; and
   (2) a second leaflet of the plurality of leaflets is interposed between an outer surface of a second finger of the plurality of axially-extending fingers and an inner surface of the frame, such that, along a defined radial distance from the axis extending through the shaft of the crimping accessory device, the second leaflet is adjacent to an outer surface of a second finger of the plurality of axially-extending fingers and is adjacent to an inner surface of the frame, wherein the second finger is formed from a resilient material, and the second finger is deflected radially-inwardly and exerts a radially-outwardly directed force against the inner surface of the second leaflet.

2. The assembly of claim 1, further comprising:
   a hook formed on an outer surface of the first axially-extending finger at a location spaced apart proximally from a distal end of the first axially-extending finger, at least a portion of the hook extending about the outer surface of the frame.

3. The assembly of claim 2, wherein the hook engages a portion of the annular frame.

4. The assembly of claim 3, wherein the portion of the annular frame is received by an aperture defined by a radially-inner surface of a portion of the hook spaced apart from an outer radial surface of the shaft.

5. The assembly of claim 4, the portion of the hook extending longitudinally, distally, and parallel to, an outer surface of the shaft.

6. The assembly of claim 4, wherein the aperture is not accessible from a proximal, longitudinal side of the hook.

7. The assembly of claim 1, the plurality of leaflets defining a plurality of leaflet commissures connected to the annular frame, wherein the plurality of leaflets are joined at respective leaflet commissures and a finger of the plurality of axially-extending fingers is disposed proximate each side of the respective leaflet commissure.

8. An assembly comprising:
a prosthetic valve comprising a radially expandable and compressible annular frame, the annular frame having an outer surface, an inner surface, and struts defining a plurality of frame windows, the prosthetic valve further comprising a leaflet assembly supported inside the annular frame, the leaflet assembly comprising a plurality of leaflets, respective leaflets of the plurality of leaflets having an inner surface and an outer surface; and
a crimping accessory device comprising an elongate shaft and a plurality of axially-extending fingers, at least a first axially-extending finger of the plurality of axially-extending fingers having a proximal portion interposed between a proximal portion of the inner surface of the annular frame and a proximal portion of the outer surface of a leaflet of the plurality of leaflets, the at least a first axially-extending finger having a distal portion extending outwardly through, and radially outwardly from, a frame window of the plurality of frame windows such that, along a defined radial distance from an axis extending through the elongate shaft of the crimping accessory device, an inner surface of the at least a first axially-extending finger is adjacent the outer surface of the first leaflet and an opposing outer surface of the at least a first axially-extending finger is adjacent the inner surface of the frame; and
a plurality of sets of axially-extending fingers formed from at least a portion of the plurality of axially-extending fingers, the at least a first axially extending finger being part of a set of the plurality of sets, given sets of the plurality of sets including at least two fingers of the plurality of axially-extending fingers, given sets corresponding to a leaflet of the prosthetic valve, given sets comprising at least one finger of the plurality of axially-extending fingers interposed between, and adjacent to, the outer surface of a leaflet of the plurality of leaflets and the inner surface of the frame, and at least another finger of the plurality of axially-extending fingers interposed inwardly of the inner surface of the respective leaflet.

9. The assembly of claim 8, wherein the at least a first axially-extending finger is formed from the elongate shaft and extends from the elongate shaft in a cantilevered manner.

10. The assembly of claim 8, wherein the at least a first axially-extending finger extends from the elongate shaft in a cantilevered manner.

11. The assembly of claim 8, wherein the elongate shaft extends through proximal and distal ends of the prosthetic valve.

12. A method for compressing a prosthetic valve, the prosthetic valve comprising a radially expandable and compressible annular frame and a leaflet assembly mounted inside of the annular frame, in cooperation with a crimping accessory device, the method comprising:
inserting each of a first group of one or more fingers of a plurality of fingers of the crimping accessory device between an inner surface of the annular frame and an outer surface of a respective leaflet such that, along a defined radial distance from an axis extending through a shaft of the crimping accessory device, an inner surface of at least one finger of the first group of one or more fingers is adjacent the outer surface of its respective first leaflet and an opposing outer surface of the at least one finger of the first group of one or more fingers is adjacent the inner surface of the frame;
placing respective fingers of a second group of one or more fingers of the plurality of fingers against an inner surface of a respective leaflet, wherein fingers of the second group are formed from a resilient material, and the fingers of the second group are deflected radially-inwardly and exert a radially-outwardly directed force against the inner surface of a respective leaflet;
placing the prosthetic valve with the inserted crimping accessory device in a crimping aperture of a crimping device formed by a plurality of circumferentially-arranged jaws of the crimping device;
at least partially crimping the prosthetic valve; and
removing the crimping accessory device from the prosthetic valve after at least partially crimping the prosthetic valve using the crimping device.

13. The method of claim 12, wherein the crimping accessory device comprises a plurality of sets of fingers, respective sets of the plurality of sets of fingers comprising at least one finger of the first group and at least one finger of the second group, each set corresponding to a leaflet of the prosthetic valve.

14. The method of claim 12, wherein at least one finger of the first group and at least one finger of the second group are circumferentially spaced apart from one another in a first set, and at least another finger of the first group and at least another finger of the second group are circumferentially spaced apart from one another in a second set, the first and second sets being spaced circumferentially further apart from one another than the spacing between the fingers within the first and second sets.

15. The method of claim 12, wherein at least one finger of the plurality of fingers comprises a hook formed on an outer surface of the at least one finger.

16. The method of claim 12, further comprising:
securing the crimping accessory device to the prosthetic valve prior to crimping or radially compressing the prosthetic valve; and
releasing the crimping accessory device from the prosthetic valve after crimping or radially compressing the prosthetic valve.

17. The method of claim 16, wherein securing the crimping accessory device to the prosthetic valve comprises coupling the crimping accessory device to the prosthetic valve using one or more lines of suture.

* * * * *